(12) United States Patent
Turp et al.

(10) Patent No.: US 8,512,746 B2
(45) Date of Patent: Aug. 20, 2013

(54) EXTENDED RELEASE PHARMACEUTICAL COMPOSITIONS OF LEVETIRACETAM

(75) Inventors: Hasan Ali Turp, Istanbul (TR); Gulay Yelken, Istanbul (TR); Asiye Sezgia, Istanbul (TR); Ali Turkyilmaz, Istanbul (TR); Levent Oner, Ankara (TR)

(73) Assignee: Sanovel Ilac Sanayi Ve Ticaret Anonim Sirketi (TR)

( * ) Notice: Subject to any disclaimer, the term of this patent is extended or adjusted under 35 U.S.C. 154(b) by 259 days.

(21) Appl. No.: 12/838,916

(22) Filed: Jul. 19, 2010

(65) Prior Publication Data

US 2011/0020445 A1 Jan. 27, 2011

(30) Foreign Application Priority Data

Jul. 22, 2009 (TR) .................................. 200905670

(51) Int. Cl.
*A61K 9/20* (2006.01)
(52) U.S. Cl.
USPC ............ 424/465; 424/464; 424/474; 424/468
(58) Field of Classification Search
None
See application file for complete search history.

(56) References Cited

U.S. PATENT DOCUMENTS

2009/0263481 A1 * 10/2009 Patil et al. ..................... 424/472

FOREIGN PATENT DOCUMENTS

| WO | WO0151033 A1 | 7/2001 |
| WO | WO2006080029 A1 | 8/2006 |
| WO | WO2006088864 A1 | 8/2006 |
| WO | WO2006123357 A2 | 11/2006 |
| WO | WO 2007054976 A2 * | 5/2007 |
| WO | WO2008006528 A2 | 1/2008 |
| WO | WO2008062446 A2 | 5/2008 |

OTHER PUBLICATIONS

European (IB) Search Report/Written Opinion for TR 200905670, Dated Feb. 8, 2010 (7 pages).
Rowe, Raymond C. et al., XP-002567254, Polymethacrylates, Handbook of Pharmaceutical Excipients, 5th Ed., pp. 554-560, Washington DC: American Pharmacists Association; 2005.

* cited by examiner

*Primary Examiner* — James H Alstrum Acevedo
*Assistant Examiner* — Daniel L Branson
(74) *Attorney, Agent, or Firm* — Hiscock & Barclay, LLP

(57) ABSTRACT

Extended release pharmaceutical compositions of levetiracetam or pharmaceutically acceptable salts thereof in the form of a tablet comprising glyceryl behenate and a polymethacrylate polymer with at least one pharmaceutically acceptable excipient.

18 Claims, No Drawings

EXTENDED RELEASE PHARMACEUTICAL COMPOSITIONS OF LEVETIRACETAM

CROSS REFERENCE TO RELATED APPLICATIONS

This application is based upon Turkish Patent Application No. TR200905670, filed Jul. 22, 2009, under relevant sections of 35 USC §119, the entire contents of this application being incorporated by reference herein.

TECHNICAL FIELD OF THE INVENTION

The present invention is related to extended release pharmaceutical compositions of levetiracetam or pharmaceutically acceptable salts thereof in the form of a tablet comprising glyceryl behenate and a polymethacrylate polymer with at least one pharmaceutically acceptable excipient.

BACKGROUND OF THE INVENTION

Levetiracetam is an antiepileptic drug available as immediate and extended release tablets for oral administration. Its chemical name is (αS)-α-Ethyl-2-oxo-1-pyrrolidineacetamide and its chemical structure is shown in the Formula I.

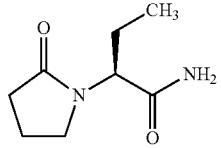

Formula I

Extended release dosage form of levetiracetam is marketed under the brand name Keppra XR™ and it is administered orally in a therapeutic dose of 500 mg and 750 mg.

Levetiracetam is indicated as adjunctive therapy in the treatment of partial onset seizures in adults with epilepsy. It is recommended that such treatments should be initiated with a daily dose of 1000 mg once daily. Additional dose increments may be given so as to reach a maximum recommended daily dose of 3000 mg. Currently commercially available tablets are available in strengths of 500 mg and 750 mg of levetiracetam, making it very inconvenient for the patient to comply with the dosing regimen prescribed, particularly when the patient may be stabilized at the higher daily dose.

Levetiracetam is a rapidly soluble active ingredient and almost completely absorbed after oral administration, so it is difficult to slow down the release without causing dose dumping and to formulate levetiracetam as an extended release pharmaceutical composition especially comprising high amounts of about 500 mg to 1500 mg per tablet for once daily or twice daily dosing.

In the prior art, there are many patents including levetiracetam in several different modified release pharmaceutical compositions, for example in PCT application, WO 2006/088864 A1, Elan Pharma Int. Ltd., Feb. 2, 2005, a controlled release composition of levetiracetam is disclosed which comprises an immediate release component and a modified release component or formulation. The modified release component or formulation is preferably in the form of an erodable formulation, a diffusion controlled formulation or an osmotic controlled formulation.

WO0151033 A1, UCB S.A., Jan. 14, 2000, provides a solid pharmaceutical compound that can be administered orally, permitting controlled release of at least one active substance which can be levetiracetam consisting of a homogeneous mixture comprising active substance, at least one matrix excipient between 5 and 95% by weight of the total weight of the compound, selected among the inert matrices, the hydrophilic, or lipid matrices, mixtures of inert and lipidic matrices mixture of hydrophilic and inert matrices; at least one entero-soluble polymer between 2 and 50% by weight of the total weight of the compound and at least one alkalinizing agent soluble in a aqueous phase under conditions of physiological pH, of at least 0.5 to 50% by weight of the total weight of the compound.

PCT application WO 2006/080029 A1, Alembic Ltd., 27.01.2005, relates to an extended release pharmaceutical composition of levetiracetam with once a day dosage regimen and the process of preparing it. The composition is preferably in the form of a coated tablet. The extended release tablet of levetiracetam with the core comprising of levetiracetam and water dispersible rate controlling polymer, and the tablet core optionally functional coated comprising a combination of water non-dispersible and/or water dispersible polymer.

PCT application WO 2006/123357 A2, Sun Pharmaceutical Industries Ltd.HHH Feb. 22, 2005, relates to an oral controlled release pharmaceutical composition in the form of a unit dosage form comprising: (a) therapeutically effective amount of levetiracetam or pharmaceutically acceptable salts thereof, and (b) a rate controlling means comprising a rate-controlling agent and/or a coating selected from a (i) active ingredient permeable coating surrounding the unit dosage form, and (ii) an active ingredient impermeable coating covering one or more surfaces but not all the surfaces of the unit dosage form, wherein the composition is in the form of a compact tablet and the levetiracetam or pharmaceutically acceptable salts thereof is present in an amount ranging from 55% to 90% by weight of the tablet.

PCT application WO 2008/006528 A2, UCB Pharma S.A., Jul. 13, 2006, discloses a prolonged release composition in the form of a tablet comprising as an active ingredient, levetiracetam, and as an excipient within the core of the tablet, 5.0 to 59.0% per weight of at least one hydrophilic matrix agent such as hydroxypropyl methylcellulose, with respect to the total weight of the core of the tablet. The most preferably the range is 25.0 to 28.0% per weight of hydrophilic matrix agent, with respect to the total weight of the core of the tablet. Furthermore, the tablet is coated with a hydrophilic polymer such as Opadry™.

Another PCT application WO 2008/062446 A2, Alembic Ltd., 14.09.2006, provides an extended release composition of levetiracetam, which exhibits no adverse food effect, comprising from about 30% w/w to about 85% w/w of levetiracetam and about 1% w/w to about 50% w/w of the composition of a water dispersible rate controlling polymer, wherein the composition is in tablet form and said tablet is coated with a functional coat of about 1% w/w to 15% w/w of the tablet weight comprising a combination of a water non dispersible polymer and a water dispersible polymer. The preffered rate controlling polymer is hydroxypropyl methylcellulose, which is in the range of 20 to 40% by weight of the total tablet composition.

These patent applications described above disclose modified release (eg. extended, prolonged, controlled release) pharmaceutical compositions of levetiracetam comprising rate controlling polymers particularly, hydroxypropyl methylcellulose which has an amount of min. 20% by weight of the total composition, and mostly have a coating and preferably the coating has one or two rate controlling agent. In this present invention, the solution to these problems described above is having a smaller quantity of the excipients and rate controlling polymers to obtain the extended release and to prevent dose dumping of pharmaceutical composition of the active ingredient, levetiracetam, such as previously not disclosed in prior art.

In this present invention, to obtain the extended release of levetiracetam, hydrophilic polymers, such as hydroxypropyl methylcellulose, are not used in high concentrations; on the other hand this may cause dose dumping. Dose dumping is one of the most important disadvantages of extended release dosage forms. Extended release formulations of highly soluble medicaments can be prone to "dose dumping" in which the release of the active ingredient is delayed, but once the release begins the medicament is released very fast. The most important criteria of dose dumping under in-vitro conditions, is the amount of the active substance released in early time point. In the prior art, to prevent dose dumping especially hydroxypropyl methylcellulose is used in high concentrations, e.g., greater than about 20% (w/w) of the dosage form and in a weight ratio greater than 1:1 relative to the drug.

Another problem is the requirement to have compact tablets that are easily swallowable; it is known that for extending the release rate of rapidly dissolved active ingredients which are also effective in higher therapeutic amounts such as levetiracetam, a large quantity of excipients are used, including the rate controlling agents. These large quantities of excipients necessary for adequate extended release of the active ingredient can make the production of the dosage form impossible or too costly. Moreover, in that case the tablet size may be too large so that the tablet cannot be swallowed.

Accordingly, a need rises for extended release formulations of levetiracetam or pharmaceutically acceptable salts thereof, which overcomes the above described problems and minimizes the adverse effects and provides a bioavailable pharmaceutical composition according to the formulations currently used. The formulation of this invention represents a novel extended release pharmaceutical composition of levetiracetam previously undisclosed in the prior art.

DESCRIPTION OF THE INVENTION

"Extended release dosage forms" are defined as systems include any dosage form that maintains therapeutic blood or tissue levels of the drug for an extended period. An extended release dosage form potentially provides greater effectiveness in the treatment of chronic conditions; greater convenience; reduces side effects and provides higher levels of patient compliance or therapeutic performance due to a simplified dosage schedule, compared with those of immediate-release drugs. Extended release pharmaceutical products are formulated to release the active ingredient gradually and predictably over a 12-hour to 24-hour period.

As used herein, the term "core of the tablet" is defined as the pharmaceutical composition without coating. All the percentages are given per weight of the total weight of the core of the tablet, except when it is written otherwise.

The main embodiment of the present invention is to provide novel extended release pharmaceutical compositions of levetiracetam or pharmaceutically acceptable salts thereof in the form of a tablet comprising rate controlling polymers with at least one pharmaceutically acceptable excipient in the core of the tablet which overcomes the above described problems in prior art and have an additive advantages over them.

According to this embodiment, the present invention relates to a pharmaceutical composition which extends the release of levetiracetam in the form of a tablet comprising, a rate controlling polymer or its mixture in an amount of 1 to 60% by weight of total composition, preferably it is 5 to 50%, more preferably it is 10 to 40% by weight of total composition.

As used herein, "rate controlling polymer" means an excipient in the final dosage form whose primary function is to modify the duration of release of the active drug substance from the dosage form. According to this embodiment, the term "rate controlling polymer" is defined as glyceryl behenate or its mixture with a polymethacrylate polymer, preferably poly(ethyl acrylate, methyl methacrylate, trimethylammonionethyl methacrylate chloride), or its mixture with a polymethacrylate polymer, preferably poly(ethyl acrylate, methyl methacrylate, trimethylammonionethyl methacrylate chloride) and hydroxypropyl methylcellulose.

The advantages of the formulations with extended release are well known by the skilled person in the art and such possibilities were already studied for the levetiracetam. However, the major difficulty of the development of such a formulation lies in the need of using at least 500 mg unit dosage of levetiracetam to obtain the necessary therapeutic activity and only a small quantity of excipient could be added not to increase the size of the pharmaceutical dosage form (eg. tablet) in order not to have problems in swallowing them. However, it is also known by the skilled person that a high soluble active ingredient requires a substantial quantity of excipients if a sufficiently extended release must be carried out.

In one aspect, one of the advantages of this extended release pharmaceutical compositions of this invention is to prevent dose dumping by using hydrophobic polymers, such as glyceryl behenate or its mixtures with other excipients. Because of using less quantity of excipients, especially rate controlling polymers, may cause dose dumping easily if not formulated appropriately. It is known that, it is difficult to develop extended release formulations of highly and rapidly soluble pharmaceuticals. It is also hard to achieve the desired dissolution profiles, in other words, the control of the release rate is difficult. Therefore, fluctuation of the active ingredient concentration in the plasma may occur which may lead to toxicity. Also, diurnal variation of the active ingredient in plasma is also possible.

In fact the risk of these disadvantages described above, a less quantity of hydrophobic polymer, such as glyceryl behenate, is used in combination with a hydrophilic polymer, such as hydroxypropylmethylcellulose, in an amount of max. 5% to obtain the extended release pharmaceutical composition of levetiracetam, and to ensure of its total release and absorption from gastro-intestinal system a smaller quantity of a polymethacrylate polymer is also added to this formulation. This enteric soluble effect is obtained by mixing the polymethacrylate polymer, preferably poly(ethyl acrylate, methyl methacrylate, trimethylammonionethyl methacrylate chloride) to active ingredient which is not previously disclosed in prior art.

In the prior art, there are many examples of enteric coatings such as coated tablets, pellets or granules, which provides the extended release from this kind of coatings. Considering the number of steps used in preparing formulations of this kind, it is not an efficient way to formulate extended released products by this kind of processes. In this present invention, surprisingly the problem is also solved by more efficient process to prepare an extended release tablet containing a matrix of a hydrophobic polymer, such as glyceryl behenate, with polymethacrylate polymer, such as poly(ethyl acrylate, methyl methacrylate, trimethylammonionethyl methacrylate chloride) as the rate controlling polymers. Moreover, it has been also sought to find a method of extending the release of the drug without placing the rate controlling polymers in a coating, but by blending them with the active ingredient, levetiracteam. In this invention the weight ratio of glyceryl behenate to poly(ethyl acrylate, methyl methacrylate, trimethylammonionethyl methacrylate chloride) is 15:1 to 1:10 (w/w), more preferably the weight ratio is 10:1 to 1:1 (w/w).

The preferred hydrophobic polymers in this invention are glyceryl behenate, glyceryl palmitostearte, glyceryl monostearate, polyglycolized glycerides hydrogenated vegetable oils such as hydrogenated castor oil, cetyl alcohol or mixtures thereof. The most preferred hydrophobic polymer is glyceryl behenate or hydrogenated castor oil.

Rate controlling polymers can be used to form a matrix in which an active substance is dispersed, the properties of the polymer are then utilized to control the rate at which the active ingredient is released from the formulation. The rate controlling polymers of this invention are selected from the group comprising glyceryl behenate, polymethacrylate polymers (eg. poly(ethyl acrylate, methyl methacrylate, trimethylammonionethyl methacrylate chloride), hydroxylpropyl methylcellulose, hydrogenated vegetable oils (eg. Hydrogenated castor oil), polyvinylpyrrolidine, polyethylene oxide, alginate salts and complex salt of alginic acid, shellac, waxes and derivatives and mixtures thereof.

In one aspect, the dissolution of levetiracetam within the rate controlling polymer matrix is enhanced by maintaining a good mixture of hydrophobic polymer, such as glyceryl behenate with other excipients such as lactose or microcrystalline cellulose. Thus, we obtain a good mixture of rate controlling polymers having a synergistic effect over the release rate of the levetiracetam. According to this aspect, the amount of lactose in this invention is 1 to 20% by weight of total composition; preferably it is 1 to 10% by weight of total composition.

In other aspect, this activity is maintained by utilizing hydrophobic and hydrophilic polymers in combination in the polymer matrix to control the release of the active ingredient for superior bioavailability. To maintain a high level of bioavailability of the active ingredient, a preferred combination of a hydrophobic with a hydrophilic polymer present in the rate controlling polymer matrix is glyceryl behenate and hydroxypropyl methylcellulose respectively. The weight ratio of glyceryl behenate to hydroxypropyl methylcellulose (HPMC) is in the range of 30:1 to 1:10; preferably it is 15:1 to 1:5, more preferably it is 5:1 to 1:1.

In another aspect, the amount of the hydrophobic polymer which is glyceryl behenate is also used less than the active ingredient, levetiracetam. It is preferred that the weight ratio of levetiracetam to glyceryl behenate ranges from 10:1 to 1:10; preferably it is 5:1 to 1:1. It is believed that the smaller amount of hydrophobic material makes the dosage form more stable and physically stronger. The concentration of hydrophobic material used is reasonably small, allowing the formation of very hard tablets.

In one aspect, the extended relase pharmaceutical composition of levetiracetam or pharmaceutically acceptable salts thereof is in the form of a tablet, multilayered tablet, pellet, granule, pill, capsule or other unit oral dosage form. The preferred unit oral dosage form is a tablet. After the tablet is formed, it may be coated with materials normally used in pharmaceutical arts. When coated, the coating is prepared by techniques known in the art, but the rate controlling polymer matrix does not present in coating.

In one of the main embodiments of this present invention, an extended release pharmaceutical composition of levetiracetam or pharmaceutically acceptable salts thereof is provided in the form of a tablet comprising glyceryl behenate and a polymethacrylate polymer with at least one pharmaceutical acceptable excipient.

In one embodiment, the extended release pharmaceutical composition of levetiracetam or pharmaceutically acceptable salts thereof is in the form of a tablet comprising glyceryl behenate, polymethacrylate polymer and hydroxypropyl methylcellulose.

In another embodiment, the extended release pharmaceutical composition of levetiracetam or pharmaceutically acceptable salts thereof in the form of a tablet comprising glyceryl behenate, polymethacrylate polymer, hydroxypropyl methylcellulose and lactose.

In one embodiment, said polymethacrylate polymer is preferably poly(ethyl acrylate, methyl methacrylate, trimethylammonioethyl methacrylate chloride).

In one embodiment, the rate controlling polymer of the extended release pharmaceutical composition of levetiracetam or pharmaceutically acceptable salts thereof in this present invention is glyceryl behenate which generally varies from 1% to 60% by weight of total composition. Preferably, it is from 5% to 50% by weight, more preferably, it is from 10% to 40% by weight of total composition.

In one embodiment, the rate controlling polymer of the extended release pharmaceutical composition of levetiracetam or pharmaceutically acceptable salts thereof in this present invention is polymethacrylate polymer generally varies from 0.5 to 20% by weight of total composition. Preferably it is 1 to 10% by weight of total composition.

In one embodiment, the rate controlling polymer of the extended release pharmaceutical composition of levetiracetam or pharmaceutically acceptable salts thereof in this present invention is hydroxypropyl methylcellulose which varies from 0.1 to 5% by weight of total composition. Preferably it is 1 to 5% by weight of total composition.

According to another embodiment, the preferred excipient of the extended release pharmaceutical composition of levetiracetam or pharmaceutically acceptable salts thereof in this present invention is lactose which varies from 1 to 20% by weight of total composition; preferably it is 1 to 10% by weight of total composition.

According to another embodiment of this invention, the amount of levetiracetam or pharmaceutically acceptable salts is 1% to 95% by weight of total composition, preferably 20% to 85%, more preferably 40% to 80%.

In a further aspect, the present invention relates to the extended release pharmaceutical composition of levetiracetam or pharmaceutically acceptable salts thereof, in an amount of 1 mg to 1500 mg, preferably it is in an amount of 500 mg to 1000 mg.

It has surprisingly found that in this extended release pharmaceutical composition having a weight ratio of levetiracetam or pharmaceutically acceptable salts to glyceryl behenate between the ranges of 10:1 to 1:10 (w/w) has a synergistic effect over the dissolution rate. Preferably the range is between 5:1 and 1:1 (w/w).

According to one aspect, in this invention the weight ratio of glyceryl behenate to poly methacrylate polymer is 15:1 to 1:10 (w/w), preferably it is 10:1 to 1:1 (w/w).

According to another aspect, the weight ratio of glyceryl behenate to hydroxypropyl methylcellulose is 30:1 to 1:10 (w/w), preferably it is 15:1 to 1:5 (w/w), more preferably it is 5:1 to 1:1 (w/w).

Another advantage of this invention is to provide an extended release pharmaceutical composition with a rate controlling polymer, wherein the maximum 30% of total amount of levetiracetam or pharmaceutically acceptable salts is released in 2 hours and 50-85% in 6 hours and at least 85% between in a period of 16 to 20 hours in 900 ml of 0.05M phosphate buffer at pH 6.0 using USP I, basket method rotating at 100 RPM.

The extended release formulations of this invention further comprising at least one pharmaceutically acceptable excipient selected from the group comprising lubricants, glidants, binders, diluents and fillers.

Suitable lubricants may comprise but are not limited to sodium stearyl fumarate, stearic acid, magnesium strearate, calcium stearate and the like and mixtures thereof; preferably sodium stearyl fumarate and/or magnesium stearate is selected.

Suitable glidants may comprise but are not limited to colloidal silicon dioxide, talc, aluminium silicate, starch and the like and mixtures thereof.

Suitable diluents and fillers may comprise but are not limited to lactose, microcrystalline cellulose, starch, talc, mannitol, glucose and the like and mixtures thereof; preferably lactose and/or microcrystalline cellulose is selected.

Suitable binders may comprise but are not limited to polymethacrylate polymers, polyvinylpyrrolidone, polyethylene glycol and the like and mixtures thereof; preferably a polymethacrylate polymer which is preferably poly (ethyl acrylate, methyl methacrylate, trimethylammonionethyl methacrylate chloride) is selected.

The extended release pharmaceutical compositions of this invention are administrated orally and in the form of a once-a-day or twice-a-day dosage regimen, which can be formulated in accordance with methods that are standard in the art.

In another embodiment, the extended relase tablets further comprise a coating layer which is 1 to 10% (w/w) of the total weight of the core of the tablet; preferably it is 1 to 5% (w/w). The coating layer preferably comprises polyvinyl alcohol, titanium dioxide, talc, lecithin, xanthan gum and the like and mixtures thereof.

The extended release pharmaceutical compositions of the present invention may be prepared by conventional technology well known to those skilled in the art, such as direct compression, dry granulation and wet granulation and the like. The manufacturing process is preferably performed by wet granulation.

The preferred wet granulation process of the present invention for preparing the extended release pharmaceutical composition of levetiracetam or pharmaceutically acceptable salts thereof comprises the following steps;
a. mixing levetiracetam or pharmaceutically acceptable salts thereof with glyceryl behenate, lactose and hydroxypropyl methylcellulose, wherein the mixing time is min. 20 minutes,
b. granulating the mixture with a poly(ethyl acrylate, methyl methacrylate, trimethylammonioethyl methacrylate chloride) with water or alcohol in the granulator, wherein the granulating time is min. 10 minutes,
c. sieving and drying the wet granules in oven or fluid bed dryer and sieving the dry granules,
d. optionally sodium stearyl fumarate is added to the blended mixture,
e. compressing the blended mixture to form tablets,
f. optionally coating said tablets.

Another preferred wet granulation process of the present invention for preparing the extended release pharmaceutical composition of levetiracetam or pharmaceutically acceptable salts thereof comprises the following steps;
a. mixing levetiracetam or pharmaceutically acceptable salts thereof with poly(ethyl acrylate, methyl methacrylate, trimethylammonionethyl methacrylate chloride), hydroxypropyl methylcellulose and lactose, wherein the mixing time is min. 20 minutes,
b. melting the glyceryl behenate between 65 and 75° C. degrees
c. granulating the powder mixture with melted glyceryl behenate with water or alcohol in the granulator
d. sieving and drying the wet granules in oven or fluid bed dryer and sieving the dry granules,
e. compressing the blended mixture to form tablets,
f. optionally coating said tablets.

Another preferred wet granulation process of the present invention for preparing the extended release pharmaceutical composition of levetiracetam or pharmaceutically acceptable salts thereof comprises the following steps;
a. mixing levetiracetam or pharmaceutically acceptable salts thereof with poly(ethyl acrylate, methyl methacrylate, trimethylammonionethyl methacrylate chloride) and granulating the mixture,
b. sieving and drying the wet granules in oven or fluid bed dryer and sieving the dry granules,
c. glyceryl behenate, hydroxypropyl methylcellulose and lactose are mixed with the dry granule mixture, wherein the mixing time is min. 60 minutes,
d. compressing the blended mixture to form tablets,
e. optionally coating said tablets.

The preferred direct compression process of the present invention for preparing the extended release pharmaceutical composition of levetiracetam or pharmaceutically acceptable salts thereof comprises the following steps;
a. mixing levetiracetam or pharmaceutically acceptable salts thereof and rate controlling polymers, preferably glyceryl behenate, poly(ethyl acrylate, methyl methacrylate, trimethylammonionethyl methacrylate chloride) and hydroxypropyl methylcellulose, with other excipients, preferably lactose, wherein the mixing time is min. 60 minutes,
b. optionally about 1% sodium stearyl fumarte is added to the blended mixture,
c. compressing the blended mixture to form tablets,
d. optionally coating said tablets.

This invention is further defined by reference to the following examples. Although the example is not intended to limit the scope of the present invention, it should be considered in the light of the description detailed above. It will be apparent to those skilled in the art that many modifications, both to materials and methods, may be practiced without departing from the scope of the invention.

Example 1

The extended release pharmaceutical composition of levetiracetam or pharmaceutically acceptable salts thereof in the form of a tablet consisting of,
1 to 95% (w/w) levetiracetam or pharmaceutically acceptable salts thereof
1 to 60% (w/w) glyceryl behenate
0.5 to 20% (w/w) eudragit RS (poly (ethyl acrylate, methyl methacrylate, trimethylammonionethyl methacrylate chloride)
0.1 to 5% (w/w) hydroxypropyl methylcellulose
1 to 20% (w/w) lactose
with respect to the total weight of the core of the tablet Example 2

The extended release pharmaceutical composition of levetiracetam or pharmaceutically acceptable salts thereof in the form of a tablet consisting of, 20 to 85 (w/w) levetiracetam or pharmaceutically acceptable salts thereof
5 to 50% (w/w) glyceryl behenate
1 to 10% (w/w) eudragit RS (poly (ethyl acrylate, methyl methacrylate, trimethylammonionethyl methacrylate chloride)
1 to 5% (w/w) hydroxypropyl methylcellulose
1 to 15% (w/w) lactose
with respect to the total weight of the core of the tablet.

Example 3

The extended release pharmaceutical composition of levetiracetam or pharmaceutically acceptable salts thereof in the form of a tablet consisting of,
40 to 80% (w/w) levetiracetam or pharmaceutically acceptable salts thereof
10 to 40% (w/w) glyceryl behenate
1 to 10% (w/w) eudragit RS (poly (ethyl acrylate, methyl methacrylate, trimethylammonionethyl methacrylate chloride)
1 to 5% (w/w) hydroxypropyl methylcellulose
1 to 15% (w/w) lactose
with respect to the total weight of the core of the tablet.

Example 4

The extended release pharmaceutical composition of levetiracetam or pharmaceutically acceptable salts thereof which is in the form of a tablet consisting of,
1 to 95 (w/w) levetiracetam or pharmaceutically acceptable salts thereof
1 to 60% (w/w) glyceryl behenate
0.5 to 20% (w/w) eudragit RS (poly (ethyl acrylate, methyl methacrylate, trimethylammonionethyl methacrylate chloride)
0.1 to 5% (w/w) hydroxypropyl methylcellulose
1 to 20% (w/w) lactose
0.1 to 2% (w/w) sodium stearyl fumarate
with respect to the total weight of the core of the tablet.

Example 5

The extended release pharmaceutical composition of levetiracetam or pharmaceutically acceptable salts thereof in the form of a tablet consisting of,
1 to 95% (w/w) levetiracetam or pharmaceutically acceptable salts thereof
1 to 60% (w/w) hydrgogenated castor oil
0.5 to 20% (w/w) eudragit RS (poly (ethyl acrylate, methyl methacrylate, trimethylammonionethyl methacrylate chloride)
0.1 to 5% (w/w) hydroxypropyl methylcellulose
1 to 20% (w/w) microcrystalline cellulose
with respect to the total weight of the core of the tablet.

The formulations of these examples are manufactured according to the process described above in the description and tablet formulations further comprise a coating layer which is 1 to 10% w/w of the total tablet weight, preferably it is 1 to 5% (w/w).

The invention claimed is:

1. The extended release pharmaceutical composition of levetiracetam or pharmaceutically acceptable salts thereof in the form of a core tablet including a rate controlling matrix, wherein said rate controlling matrix consists of glyceryl behenate, a polymethacrylate polymer, lactose and hydroxypropyl methylcellulose and in which the amount of levetiracetam is 1 to 95% by weight of the total composition, the amount of glyceryl behenate is 1 to 60% by weight of total composition, the amount of polymethacrylate polymer is 0.5 to 20% by weight of total composition, the amount of hydroxypropyl methylcellulose is 0.1 to 5% by weight of total composition and in which less than 30 percent of levetiracetam is released within about the first 2 hours to prevent dose dumping.

2. The extended release pharmaceutical composition of levetiracetam or pharmaceutically acceptable salts thereof in the form of a tablet according to claim 1, wherein said polymethacrylate polymer is poly(ethyl acrylate, methyl methacrylate, trimethylammonioethyl methacrylate chloride).

3. The extended release pharmaceutical composition of levetiracetam or pharmaceutically acceptable salts thereof in the form of a tablet according to claim 1, wherein the amount of lactose is 1 to 20% by weight of total composition.

4. The extended release pharmaceutical composition of levetiracetam or pharmaceutically acceptable salts thereof in the form of a tablet according to claim 1, wherein the amount of levetiracetam or pharmaceutically acceptable salts is 1 to 95% by weight of total composition.

5. The extended release pharmaceutical composition of levetiracetam or pharmaceutically acceptable salts thereof in the form of a tablet according to claim 4, wherein levetiracetam or pharmaceutically acceptable salts is in an amount of 1 mg to 1500 mg.

6. The extended release pharmaceutical composition of levetiracetam or pharmaceutically acceptable salts thereof in the form of a tablet according to claim 1, wherein the weight ratio of levetiracetam to glyceryl behenate is 10:1 to 1:10 (w/w).

7. The extended release pharmaceutical composition of levetiracetam or pharmaceutically acceptable salts thereof in the form of a tablet according to claim 1, wherein the weight ratio of glyceryl behenate to poly methacrylate polymer is 15:1 to 1:10 (w/w).

8. The extended release pharmaceutical composition of levetiracetam or pharmaceutically acceptable salts thereof in the form of a tablet according to claim 1, wherein the weight ratio of glyceryl behenate to hydroxypropyl methylcellulose is 30:1 to 1:10 (w/w).

9. An extended release pharmaceutical composition of levetiracetam or pharmaceutically acceptable salts thereof in the form of a tablet, said composition consisting of:
a) 1 to 95% (w/w) levetiracetam or pharmaceutically acceptable salts thereof
b) 1 to 60% (w/w) glyceryl behenate
c) 0.5 to 20% (w/w) poly(ethyl acrylate, methyl methacrylate, trimethylammonioethyl methacrylate chloride)
d) 0.1 to 5 (w/w) hydroxypropyl methylcellulose
e) 1 to 20% (w/w) lactose
with respect to the total weight of the core of the tablet.

10. An extended release pharmaceutical composition of levetiracetam or pharmaceutically acceptable salts thereof in the form of a tablet, said composition consisting of
a) 20 to 85% (w/w) levetiracetam or pharmaceutically acceptable salts thereof
b) 5 to 50% (w/w) glyceryl behenate
c) 1 to 10% (w/w) poly(ethyl acrylate, methyl methacrylate, trimethylammonioethyl methacrylate chloride)
d) 1 to 5 (w/w) hydroxypropyl methylcellulose
e) 1 to 15% (w/w) lactose
with respect to the total weight of the core of the tablet.

11. An extended release pharmaceutical composition of levetiracetam or pharmaceutically acceptable salts thereof in the form of a tablet, said composition consisting of:

a) 40 to 80% (w/w) levetiracetam or pharmaceutically acceptable salts thereof
b) 10 to 40% (w/w) glyceryl behenate
c) 1 to 10% (w/w) poly(ethyl acrylate, methyl methacrylate, trimethylammonioethyl methacrylate chloride)
d) 1 to 5% (w/w) hydroxypropyl methylcellulose
e) 1 to 15% (w/w) lactose
with respect to the total weight of the core of the tablet.

12. An extended release pharmaceutical composition of levetiracetam or pharmaceutically acceptable salts thereof in the form of a tablet, said composition consisting of:
a) 1 to 95% (w/w) levetiracetam or pharmaceutically acceptable salts thereof
b) 1 to 60% (w/w) glyceryl behenate
c) 0.5 to 20% (w/w) poly(ethyl acrylate, methyl methacrylate, trimethylammonioethyl methacrylate chloride)
d) 0.1 to 5% (w/w) hydroxypropyl methylcellulose
e) 1 to 20% (w/w) lactose
f) 0.1 to 2% (w/w) sodium stearyl fumarate
with respect to the total weight of the core of the tablet.

13. An extended release pharmaceutical composition of levetiracetam or pharmaceutically acceptable salts thereof in the form of a tablet having a rate controlling matrix, said composition consisting of:
a) 1 to 95% (w/w) levetiracetam or pharmaceutically acceptable salts thereof
b) 1 to 60% (w/w) hydrogenated castor oil
c) 0.5 to 20% (w/w) poly(ethyl acrylate, methyl methacrylate, trimethylammonioethyl methacrylate chloride)
d) 0.1 to 5% (w/w) hydroxypropyl methylcellulose
e) 1 to 20% (w/w) microcrystalline cellulose
with respect to the total weight of the core of the tablet.

14. The extended release pharmaceutical composition of levetiracetam or pharmaceutically acceptable salts thereof in the form of a tablet according to claim 1, further comprising a coating layer which is 1 to 10% (w/w) of the total weight of the core of the tablet.

15. The extended release pharmaceutical composition of levetiracetam or pharmaceutically acceptable salts thereof in the form of a tablet according to claim 14, wherein the coating layer comprises polyvinyl alcohol, titanium dioxide, talc, lecithin, xanthan gum and mixtures thereof.

16. The extended release pharmaceutical composition of levetiracetam or pharmaceutically acceptable salts thereof in the form of a tablet according to claim 1, wherein the composition including said core tablet is configured to be administrated orally daily.

17. The extended release pharmaceutical composition of levetiracetam or pharmaceutically acceptable salts thereof in the form of a tablet according to claim 1, wherein the composition is in the form of a once-a-day or twice-a-day dosage regimen.

18. The extended release pharmaceutical composition of levetiracetam or pharmaceutically acceptable salts thereof in the form of a tablet according to claim 1, including a coating layer covering said core tablet, said coating layer not including said rate controlling matrix.

* * * * *